United States Patent [19]

Iqbal et al.

[11] Patent Number: 4,490,542

[45] Date of Patent: Dec. 25, 1984

[54] 1,4-DIKETO-PYRROLO[3,4-C]PYRROLES

[75] Inventors: Abul Iqbal, Ettingen; Luigi Cassar, Kaiseraugst, both of Switzerland

[73] Assignee: Ciba-Geigy Corporation, Ardsley, N.Y.

[21] Appl. No.: 519,170

[22] Filed: Aug. 1, 1983

Related U.S. Application Data

[62] Division of Ser. No. 358,734, Mar. 16, 1982, Pat. No. 4,415,685.

[30] Foreign Application Priority Data

Mar. 20, 1981 [CH] Switzerland .......................... 1905/81

[51] Int. Cl.³ ........................................... C07D 487/08
[52] U.S. Cl. ..................................................... 548/453
[58] Field of Search ......................................... 548/453

[56] References Cited

FOREIGN PATENT DOCUMENTS 61426 9/1982 European Pat. Off. ............ 548/453

OTHER PUBLICATIONS

Farnum et al., Tetrahedron Letters, pp. 2549-2552 (1974).

*Primary Examiner*—Glennon H. Hollrah
*Assistant Examiner*—D. B. Springer
*Attorney, Agent, or Firm*—Luther A. R. Hall

[57] ABSTRACT

A process for dyeing high-molecular organic material in the bulk characterized by the use of a 1,4-diketo-pyrrole[3,4-c]-pyrrol of the formula

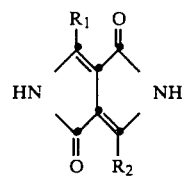

wherein $R_1$ and $R_2$ are isocyclic or heterocyclic aromatic radicals, preferably unsubstituted or substituted phenyl or naphthyl radicals.

The dyeings obtained, for example in plastics, fibres, lacquers and printings, are distinguished by very high coloring strength, high saturation, good dispersibility, good fastness to cross-lacquering, migration, heat, light and weather, and also by a high gloss and a good IR-remission behavior.

4 Claims, No Drawings

1,4-DIKETO-PYRROLO[3,4-C]PYRROLES

This is a divisional of application Ser. No. 358,734, filed on Mar. 16, 1982, now U.S. Pat. No. 4,415,685, issued on Nov. 15, 1983.

The invention relates to the dyeing of polymers with pigments. Pigments suitable for a wide field of application in polymers have to satisfy the following requirements: high purity of shade (saturation), high colouring strength, good fastness properties, especially fastness to heat, and easy availability. The red pigments customarily used at present meet some of these requirements, but none of the present red pigments offers a combination of all these good properties.

The present invention relates to a process for dyeing high-molecular organic material in the bulk and is characterised by the use of a 1,4-diketo-pyrrolo[3,4-c]-pyrrole of the formula

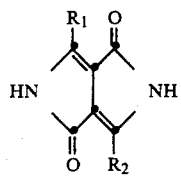

wherein
$R_1$ and $R_2$ are isocyclic or heterocyclic aromatic radicals.

The compounds of the formula (I) are red pigments which satisfy to a great extent the requirements mentioned above.

The formula (I) and also the formulae given in the following represent only one of the possible tautomeric structures.

The radicals $R_1$ and $R_2$ can be different or, preferably, identical. When $R_1$ and $R_2$ are aromatic radicals, then preferably they are mono- to tetracyclic radicals, in particular mono- or bicyclic radicals, thus phenyl, diphenylyl or naphthyl radicals. These can contain the usual non-water-solubilising substituents, such as:

(1) Halogen atoms, for example chlorine, bromine or fluorine.

(2) Alkyl groups (preferably having 1—6 C atoms): these can contain non-water-solubilising substituents, such as fluorine atoms, hydroxyl or cyano groups, or groups of the formulae —$OR_7$, —$OCOR_6$, —$COOR_6$, —$CONR_7R_8$ or —$R_6$—$OCONHR_6$ wherein $R_6$ is alkyl (preferably $C_1$–$C_6$-alkyl), aryl, for example naphthyl, or phenyl which is unsubstituted or substituted by halogen, $C_1$–$C_6$-alkyl or -alkoxy, or $R_6$ is $C_5$–$C_6$-cycloalkyl, aralkyl, particularly benzyl, or a heterocyclic radical, $R_7$ and $R_8$ are each hydrogen, alkyl (especially $C_1$–$C_6$-alkyl), $C_2$–$C_6$-cyanoalkyl or hydroxyalkyl, $C_5$–$C_6$-cycloalkyl, aryl or heteroaryl, and particularly phenyl which is unsubstituted or substituted by halogen, $C_1$–$C_6$-alkyl or -alkoxy, or wherein $R_7$ and $R_8$ together with the N atom form a 5- or 6-membered hetero ring, for example a morpholine or piperidine ring or phthalimide ring. Further substituents on the alkyl radicals are also mono- or dialkylated amino groups, especially those having 2-6 C atoms, aryl radicals, for example naphthyl radicals or in particular phenyl radicals unsubstituted or substituted by halogen, $C_1$–$C_6$-alkyl or -alkoxy, or heterocyclic aromatic radicals, for example the 2-thienyl, 2-benzoxazolyl, 2-benzthiazolyl, 2-benzimidazolyl or 6-benzimidazolonyl radicals, or the 2-, 3- or 4-pyridyl or 2-, 4- or 6- quinolyl radicals.

The following may be mentioned as unsubstituted or substituted alkyl radicals: methyl, ethyl, n-propyl, isopropyl, hexyl, propenyl, hydroxymethyl, trifluoromethyl, trifluoroethyl, cyanomethyl, methoxycarbonylmethyl, acetoxymethyl or benzyl.

(3) The group —$OR_9$, wherein $R_9$ is hydrogen, alkyl, in particular $C_1$–$C_6$-alkyl, aryl, for example naphthyl, or in particular phenyl which is unsubstituted or substituted by halogen, $C_1$–$C_6$-alkyl or -alkoxy, or $R_9$ is $C_5$–$C_6$-cycloalkyl, aralkyl or a heterocyclic radical. Examples of $R_9$ are: hydrogen, methyl, ethyl, n-propyl, isopropyl, trifluoroethyl, phenyl, o-, m- or p-chlorophenyl, o-, m- or p-methylphenyl, α- or β-naphthyl, cyclohexyl, benzyl, thienyl or pyranylmethyl.

(4) The group —$SR_9$, wherein $R_9$ has the meanings given under (3). Examples of $R_9$ are: methyl, ethyl, n-propyl, isopropyl, phenyl, o-, m- or p-chlorophenyl, o-, m- or p-methylphenyl, α- or β-naphthyl, cyclohexyl, benzyl, thienyl or pyranylmethyl.

(5) The cyano group.

(6) The group of the formula —$NR_7R_8$, wherein $R_7$ and $R_8$ have the meanings given under (2). Examples which may be mentioned are: $NH_2$, methylamino, dimethylamino, ethylamino, diethylamino, isopropylamino, β-hydroxyethylamino, β-hydroxypropylamino, N,N-bis-(β-hydroxyethyl)-amino, N,N-bis-(β-cyanoethyl)-amino, cyclohexylamino, phenylamino, N-methylphenylamino, benzylamino, dibenzylamino, piperidyl or morpholyl.

(7) The group of the formula —$COOR_6$, wherein $R_6$ has the meanings given under (2). Examples of $R_6$ are: methyl, ethyl, isopropyl, n-butyl, phenyl, benzyl or furfuryl.

(8) The group of the formula —$COR_9$, wherein $R_9$ has the meanings given under (3). Examples of $R_9$ which may be mentioned are: hydrogen, methyl, ethyl, phenyl, o-, m- or p-chlorophenyl, o-, m- or p-methylphenyl or α- or β-naphthyl.

(9) The group of the formula —$NR_{10}COR_6$, wherein $R_6$ has the meanings given under (2), and $R_{10}$ is hydrogen, alkyl, especially $C_1$–$C_6$-alkyl, aryl, for example naphthyl, or especially phenyl which is unsubstituted or substituted by halogen, $C_1$–$C_6$-alkyl or -alkoxy, or $R_{10}$ is $C_5$–$C_6$-cycloalkyl, aralkyl or the radical —$COR_6$, where two radicals —$COR_6$ together with the N atom can form a heterocyclic ring. Examples which may be given are: acetylamino, propionylamino, butyrylamino, benzoylamino, p-chlorobenzoylamino, p-methylbenzoylamino, N-methylacetylamino, N-methylbenzoylamino, N-succinimido or N-phthalimido.

(10) The group of the formula —$NR_9COOR_6$, wherein $R_6$ and $R_9$ have the meanings given under (2) and (3), respectively. The following groups may be mentioned as examples: —$NHCOOCH_3$, $NHCOOC_2H_5$ or $NHCOOC_6H_5$.

(11) The group of the formula —$NR_9CONR_7R_8$, wherein $R_9$, $R_7$ and $R_8$ have the meanings given under (3) and (2). The following Examples may be mentioned: ureido, $N_2$-methylureido, $N_2$-phenylureido or $N_2$-2',4'-dimethylphenylureido.

(12) The group of the formula —$NHSO_2R_6$, wherein $R_6$ has the meanings given under (2). The following are mentioned as examples: methanesulfonylamino, phenylsulfonylamino, p-toluylsulfonylamino or β-naphthylsulfonylamino.

(13) The groups of the formula —SO₂R₆ or SOR₆, wherein R₆ has the meanings defined under (2). The following examples may be given: methylsulfonyl, ethylsulfonyl, phenylsulfonyl, 2-naphthylsulfonyl or phenylsulfoxidyl.

(14) The group of the formula —SO₂OR₁₁, wherein R₁₁ is an aryl radical, particularly a phenyl radical unsubstituted or substituted by halogen, C₁–C₆-alkyl or -alkoxy. Examples of R₁₁ are: phenyl, o-, m- or p-chlorophenyl, o-, m- or p-methylphenyl, α- or β-naphthyl.

(15) The group of the formula —CONR₇R₈, wherein R₇ and R₈ have the meanings defined under (2). Examples which may be mentioned are: carbamoyl, N-methylcarbamoyl, N-ethylcarbamoyl, N-phenylcarbamoyl, N,N-dimethylcarbamoyl, N-methyl-N-phenylcarbamoyl, N-α-naphthylcarbamoyl or N-piperidylcarbamoyl.

(16) The group of the formula —SO₂NR₇R₈, wherein R₇ and R₈ have the meanings defined under (2). Examples which may be mentioned are: sulfamoyl, N-methylsulfamoyl, N-ethylsulfamoyl, N-phenylsulfamoyl, N-methyl-N-phenylsulfamoyl or N-morpholylsulfamoyl.

(17) The group of the formula —N=N—Q, wherein Q is the radical of a coupling component, or a phenyl radical which is unsubstituted or substituted by halogen, C₁–C₆-alkyl or -alkoxy. The following are mentioned as examples of Q: the acetoacetarylide, pyrazolyl, pyridonyl, o- or p-hydroxyphenyl, o-hydroxynaphthyl, p-aminophenyl or p-N,N-dimethylaminophenyl radicals.

(18) The group of the formula —OCOR₆, wherein R₆ has the meanings defined under (2). Examples of R₆ are: methyl, ethyl, phenyl, or o-, m- or p-chlorophenyl.

(19) The group of the formula —OCONHR₆, wherein R₆ has the meanings defined under (2). Examples of R₆ are: methyl, ethyl, phenyl, or o-, m- or p-chlorophenyl.

Of particular interest is the use of the symmetrical compounds of the formula (I) wherein R₁ and R₂ are a radical of the formula

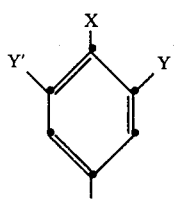

(II)

wherein X, Y and Y' are hydrogen or halogen atoms, carbamoyl, cyano, trifluoromethyl or C₂–C₆-alkylcarbamoyl groups, alkyl, alkoxy or alkylmercapto groups having 1–6 C atoms, alkoxycarbonyl or alkanoylamino groups having 2–6 C atoms, phenoxy, phenylmercapto, phenoxycarbonyl, phenylcarbamoyl or benzoylamino groups, each unsubstituted or substituted by halogen, alkyl or alkoxy having 1–6 C atoms, with at least one of the substituents X, Y and Y' being hydrogen.

Preferred are symmetrical compounds of the formula (I) wherein R₁ and R₂ are radicals of the formula

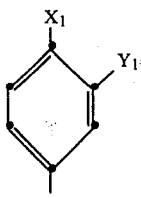

(III)

wherein one of the substituents X₁ and Y₁ is a hydrogen, chlorine or bromine atom, a methyl, cyano or alkoxy group having 1–3 C atoms, a phenoxy group which is unsubstituted or substituted by chlorine or methyl, or it is an alkoxycarbonyl or alkylcarbamoyl group having 2–5 C atoms, or a phenylcarbamoyl group which is unsubstituted or substituted by chlorine, methyl or methoxy, and the other is a hydrogen atom.

The production of the compound of the formula (I) wherein R₁ and R₂ are phenyl is described in Tetrahedron Letters No. 29, pp. 2549–52 (1974), the procedure comprising heating benzonitrile with bromoacetic ester and zinc in toluene. The remaining compounds of the formula (I) are novel, and can be produced using benzonitriles as starting materials in an analogous manner, in which process the yield can be increased by the subsequent introduction of air.

The substituents in the radicals R₁ and R₂ of the formula (I) can also be subsequently introduced, or obtained by conversion of other substituents, for example by halogenation, acylation or sulfochlorination of the compound of the formula (I), followed by reaction of the sulfochloride with amines, alcohols or phenols.

Further subject matter of the present invention is formed by the compounds of the formula

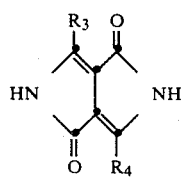

(IV)

wherein at least one of the radicals R₃ and R₄ is a substituted phenyl radical, or an (at least) bicyclic, carbocyclic aromatic radical, or a nonbasic heterocyclic aromatic radical. The radicals R₃ and R₄ can be identical or different.

Preferred compounds of the formula IV are those wherein R₃ and R₄ are identical, especially those wherein both radicals R₃ and R₄ are substituted phenyl radicals.

Preferred are those symmetrical compounds of the formula (IV) wherein R₃ and R₄ are radicals of the formula

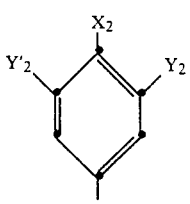

wherein $X_2$, $Y_2$ and $Y_2'$ are halogen atoms, or hydroxyl, carbamoyl, cyano, trifluoromethyl or $C_1$-$C_6$-alkylcarbamoyl groups, alkyl or alkoxy or alkylmercapto groups having 1-6 C atoms, alkoxycarbonyl or alkanoylamino groups having 2-6 C atoms, phenoxy, phenylmercapto, phenoxycarbonyl, phenylcarbamoyl or benzoylamino groups, each unsubstituted or substituted by halogen, alkyl or alkoxy having 1-6 C atoms, with at least one of the substituents $X_2$, $Y_2$ and $Y_2'$ being hydrogen.

Symmetrical compounds of the formula (IV) of particular interest are those wherein $R_3$ and $R_4$ are radicals of the formula

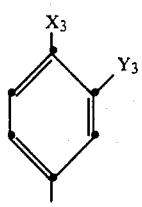

wherein one of the substituents $X_3$ and $Y_3$ is a chlorine or bromine atom, $C_1$-$C_4$-alkoxy, phenoxy unsubstituted or substituted by chlorine or methyl, or it is a methyl, cyano or $C_1$-$C_4$-alkoxycarbonyl group, and the other is a hydrogen atom.

If $R_3$ and $R_4$ are nonbasic heteroaryl radicals, then preferably they are mono- to tricyclic heteroaryl radicals. These can be purely heterocyclic, or can contain a heterocyclic ring and one or more fused-on benzene rings, which can contain the above-mentioned, non-water-solubilising substituents.

The following radicals are mentioned as examples of $R_3$ and $R_4$ in the formula (IV):
3- or 4-chlorophenyl, 3- or 4-bromophenyl, 3- or 4-fluorophenyl, 3,4- or 3,5-dichlorophenyl, 3- or 4-methylphenyl, 3- or 4-ethylphenyl, 3- or 4-isopropylphenyl, 3,4- or 3,5-dimethylphenyl, 3-chloro-4-methylphenyl, 4-chloro-3-methylphenyl, 3- or 4-methoxyphenyl, 3- or 4-ethoxyphenyl, 3- or 4-trifluoroethoxyphenyl, 3,4-dimethoxyphenyl, 3- or 4-ethoxyphenyl, 3-methyl-4-methoxyphenyl, 4-methyl-3- methoxyphenyl, 3-chloro-4-methoxyphenyl, 4-chloro-3-methoxyphenyl, 3- or 4-phenoxyphenyl, 3-chloro-4-phenoxyphenyl, 3- or 4-o-chlorophenoxyphenyl, 3- or 4-o,m, or p-methylphenoxyphenyl, 3- or 4-methylmercaptophenyl, 3- or 4-phenylmercaptophenyl, 3- or 4-cyanophenyl, 3- or 4-trifluoromethylphenyl, 3,5-bis-trifluoromethylphenyl, 4-dimethylaminophenyl, 4-diethylaminophenyl, 3- or 4-methoxycarbonylphenyl, 3- or 4-ethoxycarbonylphenyl, 3- or 4-phenoxycarbonylphenyl, 3- or 4-acetoxyphenyl, 3- or 4-benzoylphenyl, 3- or 4-benzoyloxyphenyl, 3- or 4-acetylaminophenyl, 3- or 4-benzoylaminophenyl, 3- or 4-p-chlorobenzoylaminophenyl, 4-phthaloyliminophenyl, 3- or 4-carbamoylphenyl, 3- or 4-N-methylcarbamoylphenyl, 3- or 4-N-ethylcarbamoylphenyl, 3- or 4-N-phenylcarbamoylphenyl, 3- or 4-ureidophenyl, 3- or 4-sulfamoyl- or carbamoylphenyl, 3- or 4-N-methylsulfamoylphenyl, 3- or 4-N-phenylsulfamoylphenyl, 3- or 4-methylsulfonylphenyl, 3- or 4-phenylsulfonylphenyl, 4-ureidophenyl, 4-methoxycarbonylamino, 4-alkoxycarbonylamino, 4-diphenylyl, 2-naphthyl, 9-phenanthryl, 3-pyrenyl, 2-furoyl, 2-thienyl, 6-benzofuranyl, 3,4-methylenedioxyphenyl, 4-diphenyleneoxidyl, 5-phthalimidyl, ω-naphthostyryl or 3-coumaryinyl.

The present invention relates also to a process for producing the compounds of the formula (IV) by heating a nitrile of the formula $R_3CN$, optionally together with a nitrile of the formula $R_4CN$, with bromoacetic ester and zinc in an inert organic solvent, preferably in an aromatic hydrocarbon, such as benzene, toluene or xylene.

The reaction is advantageously carried out in two stages. In the first stage, a mixture of bromoacetic ester, nitrile and zinc dust is slowly added, with the exclusion of air, to a copper-activated zinc-dust suspension in the solvent. The mixture is subsequently heated for a short time, and then optionally for a longer time with the introduction of air. The compound of the formula IV can be isolated by filtration.

Depending on the nature of their substituents and on the polymer to be dyed, the compounds of the formula I can be used as polymer-soluble dyes or in particular as pigments. In the latter case, it is advantageous to convert the products resulting from the synthesis reaction into a finely dispersed form. This can be effected in various ways, for example:

(a) By grinding or kneading, advantageously in the presence of grinding auxiliaries, such as inorganic or organic salts with or without the addition of an organic solvent. After grinding, the auxiliaries are removed in the customary manner: soluble inorganic salts for example with water, and water-insoluble organic solvents for example by means of steam distillation.

(b) By dissolving and reprecipitation from sulfuric acid, methanesulfonic acid, trichloroacetic acid or polyphosphoric acid.

(c) Conversion of the crude pigment into an alkali salt or amine salt, and hydrolysis thereof. This process is performed for example by stirring the crude pigment up with a base, for example with an alkali hydroxide or alkali alcoholate, ammonia or an amine, in a polar organic solvent, such as dimethylformamide, in the course of which the pigment goes completely or partially into solution. The pigment is precipitated by hydrolysis, preferably by acidification of the optionally filtered solution.

It can prove advantageous to subsequently treat the crude pigments, or the pigments treated according to (a), (b) or (c), with organic solvents, preferably with those boiling above 100° C. Those which prove particularly suitable are benzenes substituted by halogen atoms, or by alkyl or nitro groups, such as xylenes, chlorobenzene, o-dichlorobenzene or nitrobenzene, and also pyridine bases, such as pyridine, picoline or quinoline, also ketones, such as cyclohexanone, ethers such as ethylene glycol monomethyl ether or -monoethyl ether, amides, such as dimethylformamide or N-methyl-pyrrolidone, as well as dimethyl sulfoxide, sulfolane, or water alone, optionally under pressure. The aftertreatment can also be performed in water in the presence of organic solvents, and/or with the addition of surface-active substances or liquid ammonia or aliphatic amines.

The pigments preferably have a BET-surface of 5-150 $m^2/g$. Pigments having a BET-surface of 5-30 $m^2/g$ tend more to be of an opaque character, whereas those having BET-surfaces of 30-150 $m^2/g$ are more inclined to be transparent. The BET-surface and the particle-size distribution can be controlled by the above-mentioned aftertreatments.

Depending on the purpose of application, it is shown to be advantageous to use the pigments as toners, or in the form of preparations.

The high-molecular organic materials to be dyed according to the invention can be of natural or synthetic origin. They can be for example: natural resins or drying oils, rubber or casein, or modified natural substances, such as chlorinated rubber, oil-modified alkyd resins, viscose or cellulose ethers or esters, such as cellulose acetate, cellulose propionate, cellulose acetobutyrate or nitrocellulose, in particular however fully-synthetic organic polymers (duroplasts and thermoplasts), such as are obtained by polymerisation, polycondensation or polyaddition. From the polymerisation resin class, there may be mentioned in particular: polyolefins, such as polyethylene, polypropylene or polyisobutylene, also substituted polyolefins, such as polymers from vinyl chloride, vinyl acetate, styrene, acrylonitrile of acrylic acid and/or methacrylic acid esters, or butadiene, as well as copolymers of the desired monomers, especially ABS or EVA. From the series of polyaddition resins and polycondensation resins are mentioned the condensation products of formaldehyde with phenols, the so-called phenoplasts, and the condensation products of formaldehyde with urea, thiourea and melamine, the so-called aminoplasts, the polyesters used as lacquer resins, namely, both saturated resins, for example alkyd resins, and unsaturated resins, for example maleic resins; and also the linear polyesters and polyamides or silicones.

The high-molecular compounds mentioned can be used singly or in admixture, as plastic mixtures or melts, which can be optionally spun into filaments. They can also be used in the form of their monomers, or in the polymerised state in the dissolved form as film formers or binders, for lacquers or printing inks, for example linseed oil varnish, nitrocellulose, alkyd resins, melamine resins and urea-formaldehyde resins or acrylic resins.

The pigmenting of the high-molecular organic substances with the pigments of the formula I is performed for example by mixing a pigment of this type, optionally in the form of master batches, with the said substrates by means of roll mills or mixing and grinding apparatus. The pigmented material is subsequently processed into the desired final form by methods known per se, such as by calendering, moulding, extrusion, brushing, casting or injection moulding. It is often desirable, for producing non-rigid shaped articles or for reducing the brittleness of the products obtained, to incorporate into the high-molecular compounds, before the shaping operation, so-called plasticisers. These can be for example esters of phosphoric acid, phthalic acid or sebacic acid. In the process according to the invention, the plasticisers can be worked into the polymers before or after incorporation of the pigment dye. It is also possible, for the purpose of obtaining various shades of colour, to add to the high-molecular organic materials, in addition to the compounds of the formula I, also fillers, or other colour-imparting constituents, such as white, coloured or black pigments, in any required amounts.

For pigmenting lacquers and printing pastes, the high-molecular organic materials and the compounds of the formula I, optionally together with additives, such as fillers, other pigments, siccatives or plasticisers, are finely dispersed or dissolved in a common organic solvent or solvent mixture. It is also possible to firstly disperse or dissolve the individual constituents each on its own or several jointly, and to subsequently combine all the components.

The dyeings obtained, for example in plastics, fibres, lacquers or printings, are distinguished by a yellow to violet shade, very high colouring strength, high saturation, good dispersibility, good fastness to crosslacquering, migration, heat, light and weather, and also by a high gloss and a good IR remission behaviour. Of particular interest are the red pigments according to the invention by virtue of their neutral shade combined with a high colouring strength, saturation and good fastness properties.

The compounds of the formula (I) can also be used as photoelectrophoretic toners.

When the compounds of the formula (I) are dissolved in the applied polymers, they are likewise distinguished by a pure shade, high colouring strength and good fastness to light, and in addition by high fluorescence. They are suitable for use in solar energy collectors, and for the production of laser beams.

Except where otherwise stated in the following Examples, 'parts' are parts by weight, percentages are percent by weight, and temperature values are in degrees Centigrade.

EXAMPLE 1

(soft polyvinyl chloride)

0.6 g of the pigment of the formula I ($R_1 = R_2 = phenyl$) is mixed with 67 g of polyvinyl chloride 33 g of dioctylphthalate, 2 g of dibutyltin dilaurate and 2 g of titanium dioxide, and the mixture is processed, on a roll mill for 15 minutes at 160° C., into the from of a thin sheet. The red dyeing thus produced is deeply coloured and is fast to migration and to light.

EXAMPLE 2

(hard polyvinyl chloride)

0.1 part of the pigment of the formula (I) ($R_1 = R_2 = $ phenyl) and 1 part of titanium dioxide (Rutil, stabilised) are incorporated, on a two-roller mill for 8 minutes at a rolling temperature of 160° C. and a friction value of 1:1.2, into 100 parts of a hard PVC mixture consisting of 100 parts of a PVC mass polymerisation polymer, k value 70, 3 parts of barium cadmium stearate, 1 part of tertiary organic phosphite, 1 part of octylethoxy stearate and 0.3 part of hydroxystearic acid. The dyed hard PVC hide is taken off the roller mill and moulded for 5 minutes at 160° C. on a multiplaten press. The specimen plate obtained is distinguished by a very brilliant red shade.

EXAMPLE 3

(polyethylene)

0.2 part of the pigment of the formula (I) ($R_1 = R_2 = $ phenyl), 1 part of titanium dioxide (Rutil) and 100 parts of LD polyethylene granulate are mixed in a drum mixer, and the mixture is subsequently processed on mixing rolls at 130° C. The mixture is moulded hot into the form of plates, or is formed in an extruder. The plates display a beautiful red dyeing having good fastness to light.

EXAMPLE 4

(polypropylene)

0.1 part of the pigment of the formula (I) $R_1 = R_2 = $ phenyl), 0.5 part of titanium dioxide (Rutil)

and 100 parts of polypropylene granulate are mixed in a drum mixer, and the mixture is subsequently processed at 90° C. on mixing rolls until a homogeneously dyed mixture is obtained. This is then moulded hot into the form of plates 1 mm thick. The plates display a beautiful red shade having good fastness to light.

EXAMPLE 5

(polystyrene)

0.05 part of the pigment of the formula I ($R_1=R_2=$phenyl) is mixed dry with 100 parts of polystyrene. The mixture is kneaded at a temperature of between 200° and 280° C. until a homogeneous dying is obtained. The dyed mixture is left to cool, and is then ground in a mill to obtain a particle size of about 2 to 4 mm. The resulting granulate is processed in an injection moulding machine at temperatures of between 220° and 300° C. into the form of moulded articles. The products have been dyed in a red shade and have good fastness and temperature stability.

EXAMPLE 6

(polymethylmethacrylate)

0.02 part of the pigment of the formula I ($R_1=R_2=$p-chlorophenyl) is mixed dry with 100 parts of polymethylmethacrylate, and the mixture is homogenised in a two-spindle extruder. The material emerging from the opening of the extruder is granulated, and can then be moulded into shapes in the customary manner. A plastics material dyed in a red shade is obtained.

EXAMPLE 7

(polyacrylonitrile)

1 part of the finely divided pigment of the formula (I) ($R_1=R_2=$phenyl) is added to a solution of 165 parts of polyacrylonitrile in 834 parts of dimethylformamide. The spinning solution thus obtained is pressed through a nozzle into a precipitating bath consisting of water at 90° C. The result is a fibre dyed in a red shade, which has excellent fastness to light, washing and chlorite.

EXAMPLE 8

(polyamide)

99.5 parts of a polyamide from ε-caprolactam in the form of chips are sprinkled dry with 0.5 part of a very finely divided pigment of the formula (I) ($R_1=R_2=$phenyl). The chips dusted in this manner are spun in the customary manner, for example in the coiled grid spinning process, at about 280° to 285° C. The resulting fibre material has been dyed yellow, it fluoresces and has good fastness to light and to wet processing.

EXAMPLE 9

(polyethylene terephthalate)

99.9 parts of polyethylene terephthalate granulate are shaken, for 15 minutes on a shaking machine, with 0.1 part of the pigment of the formula (I) ($R_1=R_2=$p-methylphenyl). The uniformly dyed granulate is spun at 285°±3° C., on a melt spinning machine, into the form of fibres. The fibres obtained have been dyed yellow and are distinguished by a full pure shade, brilliance and good fastness properties.

EXAMPLE 10

(polycarbonate)

0.05 part of the pigment of the formula (I) ($R_1=R_2=$phenyl) is mixed dry with 100 parts of polycarbonate from 2,2(4,4'-dioxydiphenyl)-propane having a K value of about 50, and the mixture is homogenised in a twin-screw extruder at 280° C. A transparent yellow dyeing having good fastness to light is obtained. The granulated product can be processed, by customary methods of thermoplastic deformation, for example in the injection moulding process, into shaped articles.

EXAMPLE 11

(nitrocellulose)

40 parts of a nitrocellulose lacquer, 2.375 parts of titanium dioxide and 0.125 part of the pigment of the formula (I) $R_1=R_2=$phenyl) are ground for 16 hours in a bar mill. The resulting lacquer is spread in a thin layer over an aluminium sheet. The result is a red lacquer coating having very good fastness properties.

EXAMPLE 12

(cellulose acetate)

A mixture of 25 parts of the pigment of the formula (I) ($R_1=R_2=$phenyl), 1.25 parts of cellulose acetate (54.5% of bound acetic acid), 100 parts of sodium chloride and 50 parts of diacetone alcohol is treated, with cooling, in a kneader until the desired degree of fineness of the pigment is obtained. There are then added 25 parts of water, and kneading is continued until a finely granular mixture is obtained. This is placed onto a suction filter and the sodium chloride and diacetone alcohol are completely washed out with water. The material is then dried in a vacuum chanber at 85° C. and subsequently ground in a hammer mill. 1.33 parts of the pigment preparation obtained are added to an acetate silk spinning solution consisting of 100 parts of cellulose acetate and 376 parts of acetone. The mixture is stirred for 3 hours, which suffices to ensure a complete dispersion of the dye. The filaments obtained from this mixture in the usual manner by the drying process display a red dyeing having very good fastness to light, washing and hypochlorite.

EXAMPLE 13

(viscose)

4.8 parts of the pigment of the formula (I) ($R_1=R_2$ =phenyl) are ground, in one of the known colloid mills, with 4.8 parts of the sodium salt of 1,1'-dinaphthylmethane-2,2'-disulfonic acid and 22.1 parts of water until all dye particles are smaller than 1μ. The resulting pigment suspension has a pigment content of about 15%. When this aqueous solution is added to the viscose spinning solution, there are obtained, using the customary spinning process, cellulose filaments which are dyed in a red shade and which have good fastness to light and to hypochlorite.

EXAMPLE 14

(abietic acid)

A mixture of 50 parts of the pigment of the formula (I) ($R_1=R_2=$phenyl), 100 parts of Staybelite Ester 10 (glycerol ester of hydrogenated colophonium), 200 parts of sodium chloride and 18 parts of diacetone alcohol is treated, with cooling, in a kneader until the desired degree of finess of the pigment is obtained. The sodium chloride and diacetone alcohol are then removed from the kneaded mixture by the introduction of water at 80° C. The kneaded mixture itself remains intact. The salt- and solvent-free kneaded product is completely dried by heating of the kneader with steam, and subsequently pulverised after cooling in the kneader. The preparation can be used for example for dyeing lacquers. For this purpose, the preparation is advantageously slurried with some toluene, and the resulting paste is stirred up with the lacquer.

EXAMPLE 15

(urea-formaldehyde resin)

100 parts of a pulverulent formaldehyde-urea resin suitable for moulding compounds, 10 parts of lithopone and 1 part of the pigment produced according to Example 1 are ground in a ball mill for 16 hours, and the mixture is subsequently pressed at 140°–160° C. into moulds. The red moulded specimens have good fastness to light and to heat.

EXAMPLE 16

(urea-formaldehyde lacquer)

15 parts of a collodion wool containing 35% of butanol, 15 parts of a phthalate resin modified with castor oil, 15 parts of a 70% butanolic solution of a urea lacquer resin, 20 parts of butyl acetate, 10 parts of glycol monoethyl ether, 20 parts of toluene and 5 parts of alcohol are processed into a lacquer. This is subsequently pigmented with 2 parts of the pigment of the formula (I) ($R_1=R_2=$phenyl) and 2 parts of titanium dioxide (Rutil) and then ground. After the lacquer has been sprayed onto cardboard and dried, the result is a red coating having very good fastness to light, cross-lacquering and weather.

EXAMPLE 17

(alkyd-melamine stoving lacquer)

60 parts of a 60% solution of a non-drying alkyd resin in xylene (trade name Beckosol 27-320, Reichhold-Albert-Chemie), 36 parts of a 50% solution of a melamine-formaldehyde resin in a butanol/xylene mixture (trade name Super-Beckamin 13-501, Reichhold-Albert-Chemie), 2 parts of xylene and 2 parts of methyl cellosolve are mixed together, and 100 parts of this mixture are stirred up, with the aid of a stirrer, to obtain a homogeneous lacquer solution. 95 parts of the clear lacquer thus obtained and 5 parts of the pigment of the formula (I) ($R_1=R_2=$phenyl) are ground in a ball mill for 72 hours. The dyed lacquer is then applied, using a customary spraying method, onto metal sheet, and subsequently stoved at 120° C. for 30 minutes. The result is a lacquering having good fastness to light.

EXAMPLE 18

(acrylic-melamine resin stoving lacquer)

41.3 parts of a 60% solution of an acrylic resin in xylene (trade name Viacryl VC 373, Vianova), 16.3 parts of a 55% solution of a melamine-formaldehyde resin in butanol (trade name Maprenal TTX, Bayer), 32.8 parts of xylene, 4.6 parts of ethyl glycol acetate, 2 parts of cyclohexanone, 2 parts of butyl acetate and 1 part of silicone oil A (1% in xylene) (Bayer) are stirred up, by means of a stirrer, to give a homogeneous lacquer solution. 95 parts of the clear lacquer thus obtained, 5 parts of the pigment of the formula (I) ($R_1=R_2=$phenyl) are ground in a ball mill for 72 hours. The dyed lacquer is then applied, by the usual spraying method, to metal sheet, and stoved at 120° C. for 30 minutes. A red lacquering having good fastness to light is obtained.

EXAMPLE 19

(letterpress printing)

1.0 g of the pigment of the formula (I) ($R_1=R_2=$p-chlorophenyl) is finely ground, on an Engelsmann grinding machine, with 4.0 g of lithographic varnish of the following composition:

| | |
|---|---|
| 29.4% of linseed oil-stand oil | (300 poise), |
| 67.2% of linseed oil-stand oil | (20 poise), |
| 2.1% of cobalt octoate | (8% Co) and |
| 1.3% of lead octoate | (24% Pb), | and then printed, by means of a cliché in the letterprinting process, with 1 g/m² onto art printing paper. A strong red shade having good transparency and a high gloss is obtained.

The pigment is suitable also for other printing processes, such as intaglio printing, offset printing and flexographic printing, and yields in these processes too likewise very good results.

EXAMPLE 20

1 part of $Cu(OOCCH_3)_2.H_2O$ is dissolved, in an Erlenmeyer flask, in 25 parts by volume of glacial acetic acid at 90° C., and 17.97 parts of zinc dust (0.274 mol) are then added. The whole mixture is well stirred for 1 minute, and subsequently filtered, and washed with a small amount of glacial acetic acid and 75 parts by volume of xylene. The thus activated zinc is placed immediately into a sulfonating flask with 40 parts by volume of xylene. There are then added dropwise, in an argon protective-gas atmosphere, 15–20 parts by volume of a mixture of 60 parts by volume of xylene, 28 parts by volume of benzonitrile (0.27 mol) and 30.4 parts by volume of ethyl bromoacetate (0.27 mol). The mixture is slowly heated to 60° C., in the course of which an exothermic reaction occurs and the temperature of the contents of the flask rapidly rises to about 90° C. The temperature from then on is maintained at ~90° C. by regulating the dropping rate of the remaining benzonitrile/ethyl bromoacetate solution. After completion of the dropwise addition, the reaction mixture is stirred at 90°–95° C. for half an hour. The argon is subsequently removed, and air is introduced into the mixture, which is refluxed and stirred for a further 10 hours at the same temperature. The mixture is then cooled to about 70° C., and approximately 100 parts by volume of acetone are added. The product which has precipitated is filtered off at room temperature, washed with methanol, and dried overnight at 80° C. in vacuo. The yield is 10.16 parts of a crude product. Three parts of this crude product are stirred in 100 ml of dimethylformamide with about 1.8 parts by volume of 30% sodium methylate solution for 2 hours at room temperature. After filtering until clear, there are added to the filtrate 3 parts by volume of glacial acetic acid and afterwards 13 parts by volume of water, and the whole is stirred overnight at room temperature. On the following morning, the precipitate is filtered off, washed with dimethylformamide, ethanol, water and ethanol in turn, and dried overnight at 80° C. in vacuo. The yield then is 1.5 parts of the compound of the formula I ($R_1=R_2=$phenyl) in the form of red powder having a BET surface of 12 m$^2$/g.

Microanalysis: $C_{18}H_{12}N_2O_2$ mol.wt. 288.3: calculated: C 74.99%; H 4.22%; N 9.72%; found: C 75.0%; H 4.4%; N 9.8%.

UV spectroscopic analysis: (solvent: N-methylpyrrolidone) $\lambda_{max}$ 504 nm; $\epsilon_{max}$ 33,000.

The above pigment dyes plastics and lacquers in pure opaque scarlet shades having excellent fastness to light, heat and weather.

EXAMPLE 21

8.8 parts (0.135 mol) of zinc dust are added to a well-stirred solution, at 90°–95° C., of 0.5 part of copper acetate.H$_2$O in 12.5 parts by volume of glacial acetic acid. After one minute, the formed sludge is allowed to settle for one minute, and the glacial acetic acid is decanted as fully as possible. The residue is washed once with 12.5 parts by volume of glacial acetic acid, and then three times with 25 parts by volume of xylene each time. The grey sediment remaining behind is placed together with 65 ml of xylene and 18.6 parts (0.135 mol) of p-chlorobenzonitrile into a sulfonating flask. The mixture is heated to ~70° C., and there are subsequently added dropwise 15 parts by volume of ethyl bromoacetate in the course of about 30 minutes, in such a manner that the temperature of the contents of the flask does not exceed 80°–85° C. After completion of the dropwise addition, refluxing is performed and, with the introduction of air, the reaction mixture is stirred overnight at the same temperature. On the following morning, the mixture is cooled to room temperature, and 50 parts by volume of acetone are added with stirring. The precipitate is filtered off after about 15 minutes, and the suction-filter residue is washed with acetone. The resulting crude product is placed into 250 parts by volume of DMF; 5 parts by volume of 30% sodium methylate solution are added, and the whole is stirred for 5 minutes. After filtration until clear, the alkaline pure dimethylformamide solution is acidified with 8 parts by volume of glacial acetic acid, and diluted with 30 parts by volume of water, and is stirred overnight at room temperature. The red precipitate is filtered off, washed with methanol, and dried at 80° C. overnight in vacuo. The yield is 3.6 parts by volume (15% of theory) of the compound of the formula I ($R_1=R_2=$p-chlorophenyl) in the form of red powder.

Elementary analysis: $C_{18}H_{10}Cl_2N_2O_2$ mol.wt. 357.21: calculated: C 60.53% H 2.82%; N 7.84%; O 8.96%; Cl 19.85% found: C 60.0% H 2.8%; N 7.7%; O 9.6%; Cl 19.6%.

UV spectroscopic analysis: (solvent: N-methylpyrrolidone) $\lambda_{max}$ 514 nm; $\epsilon_{max}$ 33,000.

The above compound dyes plastics and lacquers in pure, deeply coloured, bluish-red shades having excellent fastness to light, weather and heat.

EXAMPLE 22

By using m-chlorobenzonitrile in place of p-chlorobenzonitrile in Example 21, with otherwise an analogous procedure, there are obtained 4 g of a crude pigment, which is treated as follows in Example 23.

EXAMPLE 23

Alkaline dissolving and reprecipitation 4 parts of the above crude pigment are suspended in 135 parts by volume of dimethylformamide; 2.5 parts by volume of 30% sodium methylate solution are then added, and stirring is continued at room temperature for 2 hours. The solution is subsequently filtered clear through "Highflow", and the filtrate is neutralised with 4 parts by volume of glacial acetic acid. 18 parts of water are added, and the resulting suspension is stirred overnight at room temperature. The pigment which has precipitated is filtered off, washed firstly with a little dimethylformamide and then with water and ethanol, and dried overnight at 80° C. in vacuo. The yield is 2.4 parts of an orange-red powder of the formula I ($R_1=R_2=$m-chlorophenyl).

Microanalysis: $C_{18}H_{10}Cl_2N_2O_2$ mol.wt. 357.2: calculated: C 60.53%; H 2.82%; Cl 19.85%; N 7.84%; found: C 60.00%; H 2.80%; Cl 19.90%; N 7.80%.

UV spectroscopic analysis: (solvent: N-methylpyrrolidone) $\lambda_{max}$: 512 nm; $\epsilon_{max}$: 27,000.

The above pigment resulting from alkaline dissolving and reprecipitation dyes plastics and lacquers in pure orange shades having good fastness to migration, light and heat.

EXAMPLE 24

Acid dissolving and reprecipitation 1.4 parts of the product which has undergone alkaline dissolving and reprecipitation are suspended in 70 parts by volume of concentrated sulfuric acid, and the suspension is stirred for about 45 minutes at room temperature. After subsequent filtration until clear through "Highflow" (glass frit), the filtrate is poured into about 300 parts of ice and stirred for 15 minutes at room temperature. The pigment which has precipitated is filtered off, washed with water and ethanol, and dried overnight at 80° C. in vacuo. The yield is 1.2 parts of a red powder, which gives the same microanalytical, mass- and UV-spectroscopic data and has the same chemical structure as the pigment obtained by alkaline dissolving and reprecipitation according to Example 23. There are obtained however, on incorporation of the present acidically dissolved and reprecipitated product into plastics and lacquers pure scarlet (instead of orange) dyeings likewise having excellent pigment fastness properties.

The X-ray diffraction pattern of the pigment obtained according to Example 24 exhibits, at an interplanar spacing of 3.22 Å, a line of very strong intensity, at 14.3, 6.7 and 3.45 Å, lines of very strong intensity, at 4.72, 4.20, 3.51 and 3.35 Å, lines of medium intensity, at 5.3 and 2.98 Å, lines of weak intensity, and at 3.15 Å, a line of very weak intensity. The X-ray diffraction pattern of the pigment obtained according to Example 23 exhibits at 14.2 and 3.7 Å, lines of very strong intensity, at 4.72 Å, a line of strong intensity, at 3.52 Å, a line of medium intensity, and at 6.9 Å, a line of weak intensity.

EXAMPLE 25

When the procedure is carried out analogously to that of Example 24, using however the product obtained by alkaline dissolving and reprecipitation according to Example 20, there is obtained a very deeply coloured, transparent red pigment having a specific surface according to BET of 110 m$^2$/g.

EXAMPLE 26

If the amount of p-chlorobenzonitrile used in Example 21 is replaced by an equimolar mixture of p-chlorobenzonitrile and p-methylbenzonitrile, the procedure and processing being otherwise analogous, there is obtained a red pigment mixture, which contains, according to elementary and mass spectroscopic analysis, besides the pigments of the formula I (R₁=R₂=p-chlorophenyl), (R₁=R₂=p-methylphenyl), also the compound of the formula I (R₁=p-chlorophenyl, R₂=p-toluyl).

Mass spectroscopy: MS: M+: 336.

The above pigment mixture dyes plastics and lacquers in red shades of high saturation and with excellent fastness properties.

EXAMPLES 27–33

There are obtained analogously to Example 20 further pigments of the formula

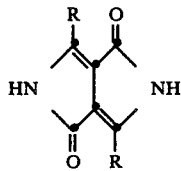

by reacting a nitrile of the formula

R—CN with ethyl bromoacetate in the presence of Zn-Cu, wherein R has the meanings given in column 2 of Table 1. Column 3 shows the shade of the dyeing in polyvinyl chloride, and column 4 contains the spectroscopic data for the pigments.

TABLE 1

| Example No. | R | Shade in PVC | λmax* nm |
|---|---|---|---|
| 27 |  (4-Cl-phenyl) | orange | 512 / 476 |
| 28 | H₃C—phenyl | red | 507 / 472 |
| 29 | NC—phenyl | claret shade | 535 / 500 |
| 30 | (CH₃)₂N—phenyl | reddish-violet | 554 / 512 |
| 31 | CH₃-phenyl | red | 505 / 470 |
| 32 | Br—phenyl | bluish-red | 515 / 480 |
| 33 | β-naphthyl | red | 526 / 491 |
| 34 | 3-trifluoromethylphenyl | yellowish-orange | 474 / 509 |
| 35 | 4-fluorophenyl | red | 464 / 500 |
| 36 | 4-benzoylaminophenyl | red | 474 / 510 |
| 37 | 4-tert-butyl phenyl | reddish-orange | 472 / 509 |
| 38 | 3,4-dimethylphenyl | red | 472 / 509 |

TABLE 1-continued

| Example No. | R | Shade in PVC | λmax* nm |
|---|---|---|---|
| 39 | R₁ = phenyl R₂ = p-toluyl | red | 470 / 505 |
| 40 | 4-methylsulfonylphenyl | red | 525 / 488 |
| 41 | 3-methoxycarbonylphenyl | red | 465 / 505 |
| 42 | 4-methoxycarbonylphenyl | reddish-violet | 495 / 520 |
| 43 | 3,4-dimethoxyphenyl | red | 515 / 480 |
| 44 | R₁ = p-chlorphenyl R₂ = 3,4-dichlorphenyl | red | 510 / 480 |
| 45 | 3-chloro-4-methylphenyl | red | 509 / 472 |
| 46 | 4-methoxyphenyl | red | 512 / 475 |
| 47 | 4-acetoxyphenyl | red | 505 / 472 |
| 48 | 4-acetylaminophenyl | | 525 / 485 |
| 49 | 3-cyanophenyl | red | 510 / 473 |

*All measurements were made in N—methylpyrrolidone, with the exception of Example 29, which was carried out in dimethylformamide.

What is claimed is:

1. A compound of the formula

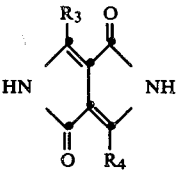

wherein R₃ and R₄ are the same and each is 1-naphthyl, 2-napthyl, 4-chlorophenyl, 3-chlorophenyl, 4-methylphenyl, 4-cyanophenyl, 4-dimethylaminophenyl, 3-methylphenyl, 4-bromophenyl, 3-trifluoromethylphenyl, 4-benzoylaminophenyl, 4-tert-butylphenyl, 3,4-dimethylphenyl, 3-methoxycarbonylphenyl, 4-methoxycarbonylphenyl, 3,4-dimethoxyphenyl, 4-methylsulfonylphenyl, 3-chloro-4-methylphenyl, 4-methoxyphenyl, 4-acetoxyphenyl, 4-acetylaminophenyl, 3-cyanophenyl, 3-bromophenyl, 4-(p-butylbenzoyloxy)phenyl, 3,5-dichlorophenyl, 3,5-dimethoxyphenyl, 4-ethoxycarbonylphenyl, 4-fluorophenyl, 4-hydroxyphenyl or 3-hydroxyphenyl.

2. A compound according to claim 1 wherein R₃ and R₄ are each 4-chlorophenyl, 3-chlorophenyl, 4-methylphenyl, 4-cyanophenyl, 3-methylphenyl, 4-bromophenyl, 3-methoxycarbonylphenyl, 4-methoxycarbonylphenyl, 4-methoxyphenyl, 3-cyanophenyl, 3-bromophenyl or 4-ethoxycarbonylphenyl.

3. A compound according to claim 2 wherein R₃ and R₄ are each 4-chlorophenyl, 3-chlorophenyl, 4-methylphenyl or 4-cyanophenyl.

4. A compound of the formula

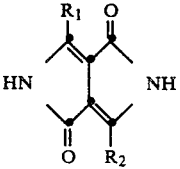

wherein
R₁ is phenyl or 4-chlorophenyl, and
R₂ is 4-methylphenyl or 3,4-dichlorophenyl.

* * * * *

UNITED STATES PATENT AND TRADEMARK OFFICE
CERTIFICATE OF CORRECTION

PATENT NO. : 4,490,542

DATED : December 25, 1984

INVENTOR(S) : Abul Iqbal and Luigi Cassar

It is certified that error appears in the above-identified patent and that said Letters Patent is hereby corrected as shown below:

Claim 1, Column 16, Line 36 should read--

2-naphthyl, 4-chlorophenyl, 3-chlorophenyl, 4-methyl- --.

Signed and Sealed this

First Day of October 1985

[SEAL]

Attest:

DONALD J. QUIGG

Attesting Officer

Commissioner of Patents and
Trademarks—Designate